United States Patent [19]
Hasson

[11] 3,948,270
[45] Apr. 6, 1976

[54] UTERINE CANNULA
[76] Inventor: Harrith M. Hasson, 345 Fullerton Parkway, Chicago, Ill. 60614
[22] Filed: Oct. 15, 1974
[21] Appl. No.: 514,409

[52] U.S. Cl. .............................. 128/348; 128/349 B
[51] Int. Cl.² ........................................ A61M 25/00
[58] Field of Search ............ 128/348, 349 R, 349 B, 128/349 BV, 350 R, 351, 246, 344

[56] References Cited
UNITED STATES PATENTS

| | | | |
|---|---|---|---|
| 2,460,473 | 2/1949 | Smith | 128/349 R |
| 2,480,041 | 8/1949 | Myller | 128/349 B |
| 2,845,930 | 8/1958 | Brown | 128/348 |
| 3,385,301 | 5/1968 | Harautuneian | 128/349 BV |
| 3,448,739 | 6/1969 | Stark et al. | 128/344 X |

FOREIGN PATENTS OR APPLICATIONS
325,740  1/1903  France ............................ 128/349 B Primary Examiner—Dalton L. Truluck
Attorney, Agent, or Firm—George H. Gerstman

[57] ABSTRACT

A uterine cannula for effecting optimum uterine fundal elevation and mobility, while minimizing the hazard of uterine injury. The instrument comprises a rigid inner tube positioned inside a Foley catheter, with the distal end of the inner tube being spaced inwardly from the open distal end of the Foley catheter. After the catheter is introduced into the endometrial cavity and the uterine fundus is reached, the Foley catheter's balloon is inflated and fluid may be injected through the rigid inner tube.

8 Claims, 5 Drawing Figures

UTERINE CANNULA

BACKGROUND OF THE INVENTION

This invention relates to a novel uterine cannula. Gynecological laparoscopy often requires uterine elevation and mobilization to selectively expose the pelvic organs and peritoneal spaces. Uterine elevation is particularly indicated in tubal sterilization and other procedures where electric cautery is used. Uterine elevation separates the uterus and adnexae from the sigmoid colon and loops of small bowel present in the pelvic cavity, and minimizes the chance of burns or other injury to these structures.

It is also possible to perform several gynecologic procedures including tubal sterilization through a small suprapubic incision, with the use of an inner uterine cannula to elevate the pelvic organs and render these organs more readily accessible to surgical manipulations. Discussion of such a procedure can be found in Saunders, W. G. and Munsick, R. A.: *Nonpuerperal Female Sterilization.* Obstet. Gynec. 40:443, 1972 and Uchida, H.: *Uchida's Abdominal Sterilization Technique.* Proceedings of the Third World Congress of Obstetrics and Gynecology. Congressprint, Vienna, 1961. Vol. 1 page 26. Advantages of this technique, as compared to conventional laparotomy, include reduced operative time with improved visualization and increased ease of manipulation, shorter hospital stay related to speedier recovery and a diminutive scar.

Several prior art instruments have been specifically designed to serve the function of uterine elevation and mobilization. These include a tenaculum attached to the cervix, a metal sound inserted into the uterus, a combination instrument of a tenaculum and sound, a large curette, a modified Fletcher after-loading tandem with Teflon guard, a vacuum uterine cannula, the Semm's vacuum cannula, the Kahn balloon cannula, and the Cohen-Eder self-retaining cannula. These instruments are generally useful, but share two distinct disadvantages.

First, the force of elevation is directed against the cervix and with the exception of the metal sound and curette only splinting of the uterine cavity is provided. The above applications are potentially safe, but do not provide adequate fundal elevation, particularly in patients with soft, retroverted uteri.

Second, uterine perforation can occur if force is inadvertently directed against the uterine corpus or fundus through the proximally protruding metal rod. Effective fundal elevation can be obtained with the use of a protruding metal rod, but the application is potentially more hazardous. Uterine perforations have been reported with the use of existing instruments.

Therefore, there is a need for a uterine cannula which is safe if a force is directed against the uterine corpus or fundus, is useful to permit uterine insufflation and injection, and also can be operated to effectively seal the cervix during insufflation and injection. It is, of course, desirable for such an instrument to be relatively inexpensive, simple to manufacture and simple to operate.

From the foregoing, it can be seen that an object of the present invention is to provide a uterine cannula which provides effective fundal elevation.

Another object of the present invention is to provide a uterine cannula which is safe and prevents uterine perforation from occurring.

A further object of the present invention is to provide a uterine cannula which has a soft end, which soft end will not pierce the uterine corpus or fundus but can be utilized for sealing the cervix.

A still further object of the present invention is to provide a uterine cannula which is simple in construction and easy to produce.

Another object of the present invention is to provide a uterine cannula which is easy to operate to provide both adequate and safe uterine fundal elevation and mobilization.

Other objects and advantages of the invention will become apparent as the description proceeds.

BRIEF SUMMARY OF THE INVENTION

In accordance with the illustrative embodiment of the present invention, a cannula is provided which comprises a conventional Foley catheter and a rigid elongated inner tube positioned inside the Foley catheter. A Foley catheter is well-known in the art, and comprises an elongated rubber tube having a balloon member concentrically positioned with respect to the rubber tube, with a device for the inflation of the balloon. The rigid elongated inner tube imparts structural rigidity to the flexible Foley catheter and carries a manually adjustable valve.

In the illustrative embodiment, the inner tube is formed of stainless steel and has an externally threaded distal end, which cooperates with an internally threaded nut for restraining the inner tube from moving within the Foley catheter.

In the operation of the invention, the rigid tube is inserted into the Foley catheter with the distal end of the rigid tube being spaced inwardly from the distal end of the Foley catheter. The catheter and the inserted tube is introduced into the endometrial cavity and the balloon is then inflated. Once the balloon is inflated, fluid may be injected through the rigid inner tube.

A more detailed explanation of the invention is provided in the following description and claims, and is illustrated in the accompanying drawings.

DETAILED DESCRIPTION OF THE ILLUSTRATIVE EMBODIMENT

Figure 1:
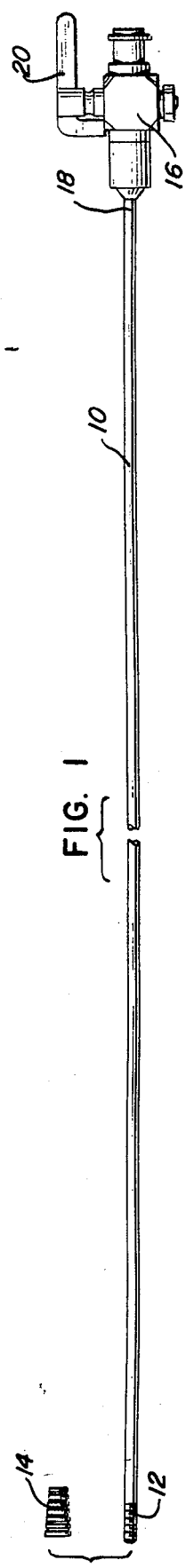
FIG. 1 is a side view of a rigid inner tube for use with the instrument of the present invention, together with a restraining nut.
Figure 2:
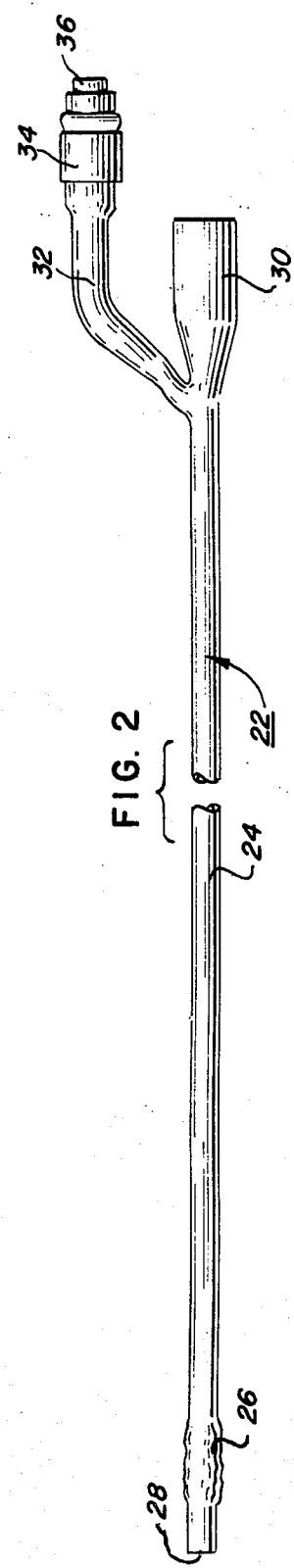
FIG. 2 is a side view of a conventional Foley catheter.

Referring to the drawings, FIG. 1 shows an inner tube 10, which is an elongated rigid tube, preferably formed of malleable stainless steel. Inner tube 10 is externally threaded at one end 12 for cooperation with an internally threaded restraining nut 14. Restraining nut 14 is frusto-conical in shape and its use will be discussed below.

A manually operable valve member 16 is connected to the other end 18 of tube 10. Valve member 16 has an internal bore that is coaxial with the bore of tube 10 and includes a manually actuable handle 20. When handle 20 is turned in a direction perpendicular to the axis of tube 10, the valve is closed and there is no flow. As the handle 20 is turned toward axial alignment with tube 10, the valve gradually opens to permit passage of fluid.

Inner tube 10 is utilized to provide structural rigidity to conventional Foley catheter 22, which is a medical device well-known in the art. Foley catheter 22 is formed of rubber and comprises an elongated flexible tube 24 carrying a balloon 26 adjacent one open end 28, with a first inlet 30 having a bore coaxial with the bore of tube 24 and a balloon operating inlet 32 having a pressure valve 34 connected adjacent its inlet 36. As can be seen with reference to FIG. 4, the bore 38 of inlet 32 communicates with a channel 40 which communicates with the inside 42 of balloon 26. Thus fluid passing into balloon 26 via bore 38 and channel 40 will tend to inflate the balloon and likewise, fluid passing from the balloon in the other direction via channel 40 and bore 38 will tend to deflate the balloon 26.

Figure 3:
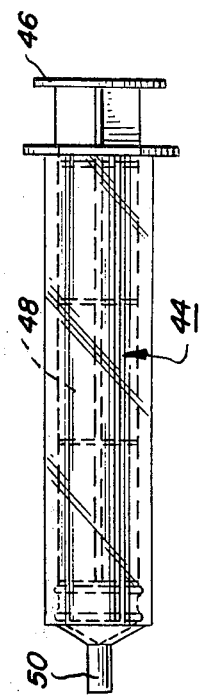
FIG. 3 is a side view of a hypodermic syringe of the type which may be used to inflate the balloon of the Foley catheter of FIG. 2.

Referring to FIG. 3, a conventional hypodermic syringe 44 is utilized to force fluid into bore 38 and to remove fluid therefrom. Syringe 44 has a handle 46 connected to a piston 48 which, when forced in the leftward direction (with respect to FIG. 3), forces fluid out of nozzle 50. Nozzle 50 is dimensioned so as to have the ability to fit into inlet 36 and to unseat the pressure valve 34. Pressure valve 34 is such that it operates only when axial pressure is exerted against it through inlet 36.

Figures 4, 5:
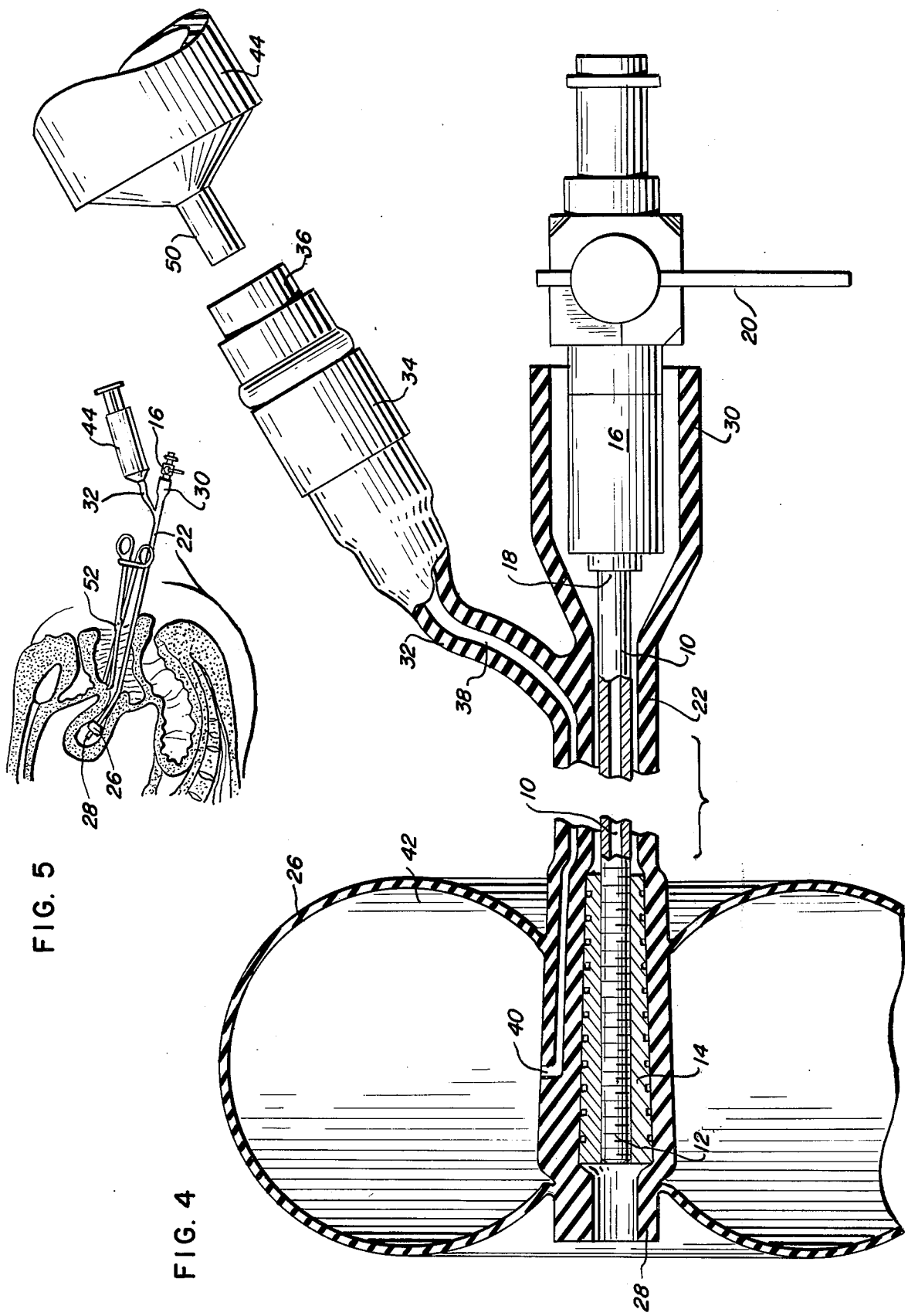
FIG. 4 is a greatly enlarged, partially broken, cross-sectional view of a uterine cannula constructed in accordance with the principles of the present invention, with the balloon being shown in its inflated condition.
FIG. 5 is a diagrammatic view of a uterine cannula constructed in accordance with the principles of the present invention being utilized with a female patient's internal structure.

To set up the instrument for use, inner tube 10 is forced into outer tube 22 by first inserting end 12 into first inlet 30 and manually moving outer tube 22 axially along inner tube 10 until first inlet 30 reaches end 18. Nut 14 is then screwed onto end 12, with the widest portion being at the distal end (as shown in FIG. 1) and then end 28 of outer tube 22 is forced over nut 14 so that end 28 is about one cm past the large end of nut 14, substantially as shown in FIG. 4. The instrument is now ready for use.

Referring to FIGS. 4 and 5, in use the patient's cervix is held with a tenaculum 52 or other holding instrument. The patient's endometrial and endocervical axial dimensions are determined, preferably by use of a Wing Sound device, known in the art. Since the conventional Foley catheter has a balloon that is two cm long, the instrument using a conventional Foley catheter should not be employed in patients having an endometrial cavity length of two cm or less. In these cases, a portion of the balloon would be contained within the cervical canal, preventing its proper distention and distorting its shape.

The device is introduced carefully into the endometrial cavity until the uterine fundus is reached. The instrument is withdrawn a fraction of a centimeter and the balloon 26 is filled with three to fifteen ml of water, until a resistance is appreciated, whichever occurs first. To fill the balloon, the syringe 44 is filled with the appropriate amount of water, nozzle 50 is inserted into inlet 36 and the syringe is operated to force water into balloon 26. In certain instances, it may be desirable to use air, or some other fluid, instead of water.

Once the balloon is filled, the tenaculum 52 is removed. The application is tested by attempting to withdraw the instrument gently from the uterus. The attempt should fail because balloon 26 should operate to seal the uterus. The uterus is then mobilized and elevated by manipulating the device.

Gas or fluid is injected through the bore of inner member 10 via valve 16. Tubal injection may be facilitated by removing the fluid from the balloon to diminish its size or by moving the balloon gently. The distended balloon effectively seals the cervix, allowing successful uterotubal injections to take place in the presence of severe cervical incompetence.

At the end of the procedure, balloon 26 is deflated by closing syringe 44, inserting nozzle 50 into inlet 36 to open valve 34 and withdrawing handle 46 to create a vacuum within the syringe and therefore withdraw the fluid from the balloon.

From the foregoing, it is seen that a novel instrument has been shown and described, which can be produced using a standard Foley catheter, is simple to use, is effective to seal the cervix and is also effective to prevent utero puncture. Although an illustrative embodiment of the invention has been shown and described, it is to be understood that various modifications and substitutions may be made by those skilled in the art without departing from the novel spirit and scope of the present invention.

What is claimed is:

1. A cannula for human uterine elevation, which comprises: a flexible, rubbery elongated outer tube carrying a balloon adjacent and encircling one open end thereof; means for inflating said balloon; a generally rigid elongated inner tube positioned inside said outer tube, means for restraining said rigid tube within said outer tube, said inner tube being positioned so that its distal end is spaced inwardly from said one end of said outer tube, said balloon being located in a position so that when said balloon is inflated, at least a portion of said balloon lies between the plane of said distal end of said inner tube and the plane of said open end; said balloon being located at a close enough distance from said open end to permit said balloon to be inflated inside the human female uterus.

2. A cannula as described in claim 1, said inflating means comprising a valve which opens only when an axial force is exerted thereagainst.

3. A cannula as described in claim 1, including a manually adjustable valve connected to the frontal end of said inner tube.

4. A cannula as described in claim 1, said inner tube being formed of stainless steel.

5. A cannula as described in claim 1, wherein said restraining means for restraining said inner tube from movement within said outer tube is positioned adjacent said one open end.

6. A cannula as described in claim 5, wherein said restraining means comprises an internally threaded nut for engaging the externally threaded distal end of said inner tube.

7. A method for human utero injection, which comprises the steps of: inserting a rigid tube into a flexible, rubbery catheter to impart structural rigidity, and securing said rigid tube within said catheter with the distal end of said rigid tube being spaced inwardly from the distal end of said catheter, said catheter carrying a balloon adjacent one open end thereof with said balloon being located in a position so that when said balloon is inflated, at least a portion of said balloon lies between the plane of said distal end of said inner tube and the plane of said open end; said balloon being located at a close enough distance from said open end to permit said balloon to be inflated inside the human female uterus; introducing said catheter and its inserted tube into the endometrial cavity; inflating the catheter's balloon while the balloon is in the uterus; and injecting fluid through the rigid tube.

8. A method as described in claim 7, and further including the step of attaching to said inner tube means for restraining said inner tube from moving within said outer tube.

* * * * *